United States Patent [19]
Morlec et al.

[11] Patent Number: 6,013,196
[45] Date of Patent: Jan. 11, 2000

[54] PROCESS AND PRODUCTS FOR DEODORISING GASEOUS COOKING EFFLUENTS

[75] Inventors: Jean Morlec, Saint Nazaire; André Deschamps, Noisy le Roi, both of France

[73] Assignee: Institute Francais du Petrole, Rueil-Malmaison Cedex, France

[21] Appl. No.: 08/972,895

[22] Filed: Nov. 18, 1997

[30] Foreign Application Priority Data

Nov. 19, 1996 [FR] France ................................. 96 14079

[51] Int. Cl.⁷ ...................................................... C09K 3/00
[52] U.S. Cl. ............................ 252/192; 422/5; 423/245.2; 424/76.1; 424/76.2
[58] Field of Search .................. 423/245.2; 422/5; 424/76.1, 76.2; 252/189, 192

[56] References Cited

U.S. PATENT DOCUMENTS

| | | | |
|---|---|---|---|
| 3,317,372 | 5/1967 | Hart | 167/14 |
| 4,070,300 | 1/1978 | Moroni et al. | 252/190 |
| 4,307,067 | 12/1981 | Tagawa et al. | 423/224 |
| 5,089,258 | 2/1992 | Zaid | 424/76.1 |

FOREIGN PATENT DOCUMENTS

| | | |
|---|---|---|
| 0 231 084 | 8/1987 | European Pat. Off. . |
| 91/12828 | 9/1991 | WIPO . |

*Primary Examiner*—Jacqueline V. Howard
*Assistant Examiner*—Cephia D. Toomer
*Attorney, Agent, or Firm*—Millen, White, Zelano & Branigan, P.C.

[57] ABSTRACT

The invention concerns a process for deodorizing malodorous gaseous effluents from cooking equipment, particularly in restaurants and in the food industry, by washing with an aqueous solution comprising an alkaline or alkaline-earth salt of a dicarboxylic acid or a polycarboxylic acid, optionally associated with a surfactant and a diholoside.

23 Claims, No Drawings

PROCESS AND PRODUCTS FOR DEODORISING GASEOUS COOKING EFFLUENTS

FIELD OF THE INVENTION

The present invention concerns a novel process for deodorizing such gaseous effluents using a washing technique which is both effective and cheap.

BACKGROUND OF THE INVENTION

Cooking equipment frequently causes an olfactory nuisance to the environment. This is particularly true for restaurants and industrial cooking equipment in the food industry, which discharge large amounts of air with a disagreeable and persistent odor.

The substances responsible for these bad odors are both numerous and not well identified: organic acids, esters, aldehydes of varying degrees of unsaturation, fats, etc. Even trace amounts can generate a disagreeable odor.

Numerous techniques for treating such discharges have been proposed to eliminate such odors. Particular examples among these are adsorption processes, for example using activated charcoal, catalytic oxidation processes, processes using solid state oxidising agents such as potassium permanganate, or oxidising agents in aqueous solution such as hydrogen peroxide, Javel water. Such processes are generally of low efficacy or are only effective for a very limited period which necessitates frequent replacement of the purifying agents and means that the treatment is very expensive.

Other processes require injecting substances which have a masking effect into the gas, but which do not actually eliminate the substances which are responsible for the bad odors. Such processes are both of low efficacy and expensive as large quantities of substances have to be continuously injected into the discharged gases.

SUMMARY OF THE INVENTION

The present invention provides a novel process for deodorizing gaseous effluents from cooking equipment, in particular in restaurants or in the food industry, characterized in that the gaseous effluent is washed, generally by contact with at least one solution which is generally aqueous comprising at least one alkaline and/or alkaline-earth salt of at least one dicarboxylic acid or a polycarboxylic acid which preferably contains 2 to 6 carbon atoms per molecule, optionally containing with at least one surfactant and at least one diholoside, preferably with a 1,6 linkage.

Examples of carboxylic acids which can be used in the present invention are dicarboxylic acids such as ethanedioic acid (oxalic acid), hexanedioic acid (adipic acid), hydroxydicarboxylic acids such as 2,3-dihydroxybutanedioic acid (tartaric acid), and hydroxytricarboxylic acids such as 2-hydroxy-1,2,3-propanetricarboxylic acid (citric acid).

They preferably contain 2 to 6 carbon atoms. Oxalic acid is a preferred acid.

These acids are generally used in the form of alkaline and/or alkaline-earth salts, preferably in the form of sodium or potassium salts, to obtain an aqueous washing solution with a pH in the range 3 to 7, preferably in the range 4 to 6.

The quantity of polycarboxylic acid salt used depends on the nature and concentration of the malodorous compounds to be eliminated. The concentration of salt in the washing water (solution) can vary within wide limits, for example between 0.01 and 10 kg/m$^3$, more generally between 0.05 and 1 kg/m$^3$.

The active substance constituted by the dicarboxylic acid or polycarboxylic acid salt described above is advantageously contain a diholoside, preferably with a 1,6 linkage, such as turanose or maltose, which reinforces the reducing nature.

Advantageously again, the active substance (diacid or polycarboxylic acid salt) can contain with a suitable surfactant, which latter has a hydrophilic-lipophilic balance (HLB) which is adjusted to encourage passage of volatile compounds into the aqueous phase and prevent deposition of fats in the washing apparatus. More generally, a polyalkylene oxide and/or polymethylsiloxane or equivalent substance is used. The ratio of the active substance (or salt) to the surfactant can vary widely, for example from 1 to 10 by weight, more particularly 2 to 4.

The different additives in the washing solution can be added separately or in a mixture, in the solid state (powder or pellets) or as a liquid (solution or suspension stabilised by a conventional homogenisina agent based, for example, on an ethylacrylate resin).

They can be added continuously or in batches.

The process of the invention can be used in all gas washers of the prior art such as packed columns, plate columns, thin film columns, bubble columns, mist contactors or any other process which ensures the best interfacial contact between the gas to be treated and the water containing the additives.

EXAMPLE 1

The effluent to be treated was constituted by the ventilating discharge from a production line for ready-cooked fish meals. The flow rate was 1100 to 1300 m$^3$/h.

The oil flow measured at the exit from the production line was of the order of 3 g per hour.

The gas was washed using a series of spray nozzles placed, as is usual, in the trajectory of the air leaving the extractor. Washing water was withdrawn in a decanting box with level control, and the remainder was recycled by a pump. Process water was introduced into the installation, depending on the flow rate of air to be treated, in a ratio which was in the range 1 to 100 ml of water per m$^3$ of gas, more generally in a ratio of 2%.

Additive DEOWASH type OX 75 is mainly constituted by a proportion of the order of 75% (by weight) of potassium tetraoxalate with a qs to 100 by weight of a crystallisable diholoside (1,6) such as maltose.

Olfactometric tests were carried out on the substance entering the washing system and on the substance after treatment.

The dilution at the "K50" olfactory perception threshold was measured. The olfaction panel was selected in accordance with standard NFX 43-101. A Proviron-Gulgues dynamic olfactometer with a single mask having three channels was used. Dilutions of 15 to 2500,000 were tested in a geometric progression with intervals of $2^{-0.5}$.

The DEOWASH additive was introduced into the washing system in a proportion of 100 g per m$^3$ of washing water.

Under these conditions, the odor flow at the inlet was 175 Nm$^3$/s. After the DEOWASH washing tower, the odor flow had been reduced to 3 Nm$^3$/s, i.e., a reduction of 98%.

EXAMPLE 2

The test of Example 1 was repeated, using DEOWASH type OX 100 constituted by pure potassium tetraoxalate in a proportion of 75 g per m$^3$ of washing water.

Under these conditions, the odour flow after the washing tower had been reduced to 20 Nm³/s, i.e., a reduction of 88.6%.

EXAMPLE 3

The effluent to be treated was constituted by the ventilation discharge from a restaurant. The nominal flow rate was 5400 Nm³/h. The effluents from the fryers in particular were filtered by an electrostatic battery.

The gas was washed with a structured packing column the water of which contained DEOWASH OX 35 additive.

The washing water was recycled at a rate of 2.5 m³/h to the head of the column through a sprinkler pipe. The packing depth and the filling density depended on the flow rates of the liquid and the gas and were determined in the normal fashion.

DEOWASH OX 35 additive is mainly constituted by a proportion of the order of 35% of the sodium salt of ethanedioic acid, about 1.5% of polymethylsiloxane, 2.5% of a polyalkylene oxide, and 5% of disodium phosphate with a qs to 100 by weight of a crystallisable diholoside with a 1–6 linkage such as turanose.

A dose of additive was introduced into the bottom of the tower in a proportion of 500 g per m³ of washing water. The washing water was recycled using a centrifugal pump. The mixture was renewed every 48 hours.

Under these conditions, the odour flow at the inlet was 1045 Nm³/s. After the DEOWASH washing tower, the odour flow had been reduced to 90 Nm³/s, i.e., a reduction of 94%.

We claim:

1. A process for deodorizing a gaseous effluent from cooking equipment in restaurants or in the food industry, comprising contacting the gaseous effluent with at least one solution comprising at least one alkaline and/or alkaline-earth salt of at least one dicarboxylic acid or a polycarboxylic acid wherein said salt is other than a salt of citric acid.

2. A process according to claim 1, wherein said at least one dicarboxylic acid or polycarboxylic acid contain 2 to 6 carbon atoms per molecule.

3. A process according to claim 1, in which the at least one solution further comprises at least one surfactant.

4. A process according to claim 1, in which the at least one solution further comprises at least one diholoside.

5. A process according to claim 4, wherein the diholoside has a 1,6 linkage.

6. A process according to claim 1, in which the dicarboxylic acid or polycarboxylic acid is selected from the group consisting of oxalic acid, adipic acid, and tartaric acid.

7. A process according to claim 1, in which the dicarboxylic acid or polycarboxylic acid is used in the form of at least one alkaline or alkaline-earth salt, so as to obtain an aqueous washing solution with a pH in the range of 3 to 7.

8. A process according to claim 7, in which the pH is in the range of 4 to 6.

9. A process according to claim 4, in which the diholoside is turanose or maltose.

10. A process according to claim 1, in which the salt concentration in said solution is in the range of 0.01 to 10 kg/m³.

11. A process according to claim 2, in which said at least one solution further comprises a surfactant.

12. A process according to claim 3, in which the salt/surfactant ratio is in the range of 1 to 10.

13. A process according to claim 11, in which the surfactant is selected from the group consisting of polyalkylene oxides and polymethylsiloxanes.

14. A process according to claim 7, wherein the acid is used in the form of a sodium or potassium salt.

15. A process according to claim 1, wherein the salt concentration is in the range of 0.05 to 1 kg/m³.

16. A process according to claim 12, wherein the ratio is 2 to 4.

17. A process according to claim 1, wherein said at least one alkaline and/or alkaline-earth salt of at least one dicarboxylic acid or a polycarboxylic acid is a salt of oxalic acid.

18. A process according to claim 17, wherein said at least one solution further comprises at least one surfactant.

19. A process according to claim 17, wherein said at least one solution further comprises at least one diholoside.

20. A process according to claim 18, wherein said at least one solution further comprises at least one diholoside.

21. A process for deodorizing a gaseous effluent from cooking equipment in restaurants or in the food industry, comprising contacting the gaseous effluent with at least one solution comprising at least one surfactant and at least one alkaline and/or alkaline-earth salt of at least one dicarboxylic acid or a polycarboxylic acid.

22. A process for deodorizing a gaseous effluent from cooking equipment in restaurants or in the food industry, comprising contacting the gaseous effluent with at least one solution comprising at least one holoside and at least one alkaline and/or alkaline-earth salt of at least one dicarboxylic acid or a polycarboxylic acid.

23. A process according to claim 21, wherein such solution further comprises at least one holoside.

* * * * *